(12) United States Patent
Shen

(10) Patent No.: US 7,031,745 B2
(45) Date of Patent: Apr. 18, 2006

(54) CELLULAR PHONE COMBINED PHYSIOLOGICAL CONDITION EXAMINATION AND PROCESSING DEVICE

(76) Inventor: Yuan-Yao Shen, 5Fl., No.8, Lane 132, Sec.2, Daan Rd., Dann Chiu, Taipei (TW)

( * ) Notice: Subject to any disclaimer, the term of this patent is extended or adjusted under 35 U.S.C. 154(b) by 310 days.

(21) Appl. No.: 10/435,080

(22) Filed: May 12, 2003

(65) Prior Publication Data

US 2004/0229661 A1 Nov. 18, 2004

(51) Int. Cl.
- H04M 1/00 (2006.01)
- A61B 5/00 (2006.01)
- A61N 1/18 (2006.01)
- A61N 1/08 (2006.01)

(52) U.S. Cl. .............. 455/550.1; 455/553.1; 600/300; 607/2; 607/60

(58) Field of Classification Search ........... 455/550.1, 455/553.1, 567, 575.1; 600/300; 607/30, 607/60, 2; 342/457; 368/10

See application file for complete search history.

(56) References Cited

U.S. PATENT DOCUMENTS

| | | | | |
|---|---|---|---|---|
| 5,626,630 A | * | 5/1997 | Markowitz et al. | 607/60 |
| 5,720,770 A | * | 2/1998 | Nappholz et al. | 607/30 |
| 5,844,522 A | * | 12/1998 | Sheffer et al. | 342/457 |
| 5,873,369 A | * | 2/1999 | Laniado et al. | 600/300 |
| 6,443,890 B1 | * | 9/2002 | Schulze et al. | 600/300 |
| 6,485,416 B1 | * | 11/2002 | Platt et al. | 600/300 |
| 6,539,253 B1 | * | 3/2003 | Thompson et al. | 607/2 |
| 6,893,396 B1 | * | 5/2005 | Schulze et al. | 600/300 |
| 2001/0014616 A1 | * | 8/2001 | Matsuda et al. | 455/567 |
| 2002/0026224 A1 | * | 2/2002 | Thompson et al. | 607/60 |
| 2002/0045804 A1 | * | 4/2002 | Christopherson et al. | 600/300 |
| 2002/0120310 A1 | * | 8/2002 | Linden et al. | 607/60 |
| 2003/0026170 A1 | * | 2/2003 | Yang | 368/10 |
| 2004/0147814 A1 | * | 7/2004 | Zancho et al. | 600/300 |

* cited by examiner

*Primary Examiner*—William Trost
*Assistant Examiner*—Kiet Doan

(57) ABSTRACT

Disclosed is a cellular phone combined physiological condition examination and processing device which can be internally integrated with or externally attached to a main circuit board of a cellular phone through system-on-a-chip, or basic frequency chip mode so as to display, indicate, store the detected physiological condition signals results on/in the cellular phone, or even transmit the detected physiological condition signals results to a remote terminal for further investigation.

10 Claims, 6 Drawing Sheets

CELLULAR PHONE COMBINED PHYSIOLOGICAL CONDITION EXAMINATION AND PROCESSING DEVICE

BACKGROUND OF THE INVENTION

1. Field of the Invention

The present invention relates to cellular phone combined physiological condition examination and processing device, more particularly, to a physiological condition examination and processing device which can be internally integrated with or externally attached to a microprocessor containing cellular phone so as to display, indicate, store the detected results on/in the cellular phone, or even transmit the detected results to a remote terminal.

2. Description of the Prior Art

Amazing advance of communication engineering has given a cellular phone variety of functions in addition to its original simple telephonic usage. Now, a cellular phone can be used as a voice recorder, a digital camera, or even can be connected to the internet for serving in many respects. As the cellular phone becomes so popular, versatile and welcome that almost everyone owns it. It seems that it is entiled to add an extra function to it.

Similarly, amazing Advance of physiological condition examination technology utilizing the modern microelectronic devices has made it possible to monitor human physiological data through skin contact, implanted biochip or detect gastric disease by using the gastroscope. How it is a fantastic dream to offer the cellular phone the function able to immediately display, indicate, store these detected data, or even transmit them remotely!

In order to realize the aforementioned dream which seems impossible, the inventor herein boldly conducted intensive research based on many years of experience gained through professional engagement in related technology with consistent experimentation and finally succeeded in materializing the present invention which will now be unveiled hereinafter.

SUMMARY OF THE INVENTION

It is an object of the present invention to provide a cellular phone combined physiological condition examination and processing device which can be internally integrated with, or externally attached to a main circuit board of a cellular phone through system-on-a-chip(SOC), or basic frequency chip mode so as to display, indicate, store the detected physiological condition signals result on/in the cellular phone, or even transmit the detected result to a remote terminal.

It is another object of the present invention that the above said human physiological examination can be performed by monitoring human physiological data through skin contact, implanted biochip, or by using a swallowed biochip to detect gastric disease utilizing the modern microelectronic devices.

It is one more object of the present invention that the data signals of above said human physiological examination can be transmitted through variety of wireless modes, such as infrared ray transmission module, blue teeth transmission module, and 820.11b module.

To achieve these and other objects mentioned above, the physiological condition examination and processing device can be internally integrated with or externally attached to a cellular phone, or built in the main board thereof by system-on-a-chip(SOC) mode. The device is composed of at least a signal receiving module, a signal processing module, and a data processing module.

The signal receiving module receives the signals of human physiological examination data from a skin surface contacting detector, an implanted biochip, or other portable measuring instruments by way of various wireless transmission modes such as, infrared ray transmission, blue teeth transmission, or 820.11b transmission. The received signals are inputted into the signal processing module.

The signal processing module converts the inputted signals from the signal receiving module into data signals and transfers said data into the data processing module.

The data processing module analyses, compares, and stores said data signals inputted from the signal processing module, and transfers the resultant data to a cellular phone functional module as an output.

Upon receiving the signals of human physiological examination data coming from outside, the signal receiving module and the data processing module proceed to carry out signal conversion, data analyzing, comparing and storing, afterwards the resultant data are displayed or indicated on, or stored in the cellular phone, or even transmitted to a remote terminal for further investigation.

BRIEF DESCRIPTION OF THE DRAWINGS

The drawings disclose the illustrative embodiments of the present invention, which serve to exemplify the various advantages and objects hereof, and are as follows:

FIG. 6 is a block diagram showing a basic frequency chip of a cellular phone in which the physiological condition examination and processing device according to the present invention is built in.

DETAILED DESCRIPTION OF THE PREFERRED EMBODIMENT

Figure 1:
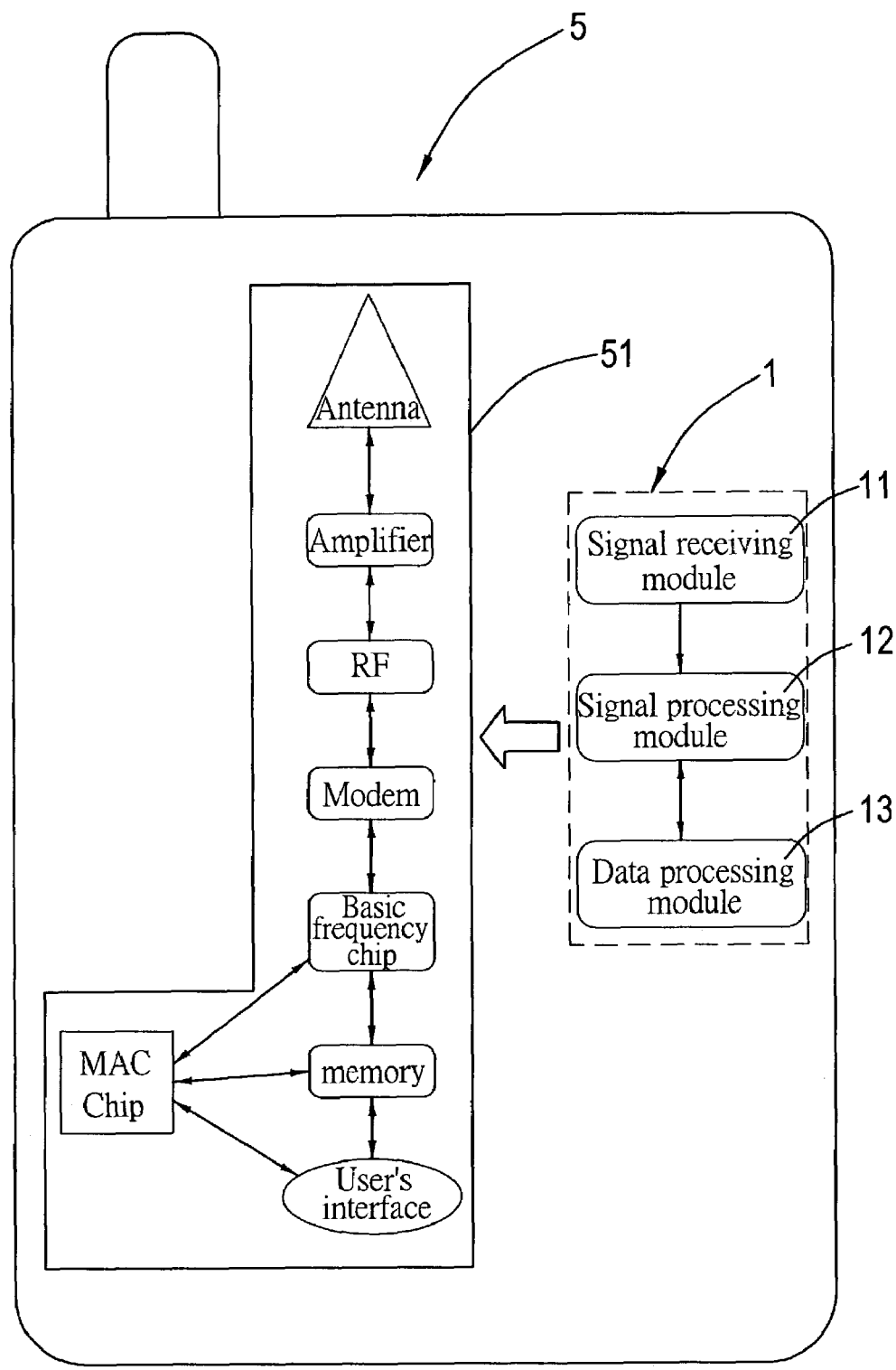
FIG. 1 is a block diagram showing the scheme of the present invention.
Figure 2:
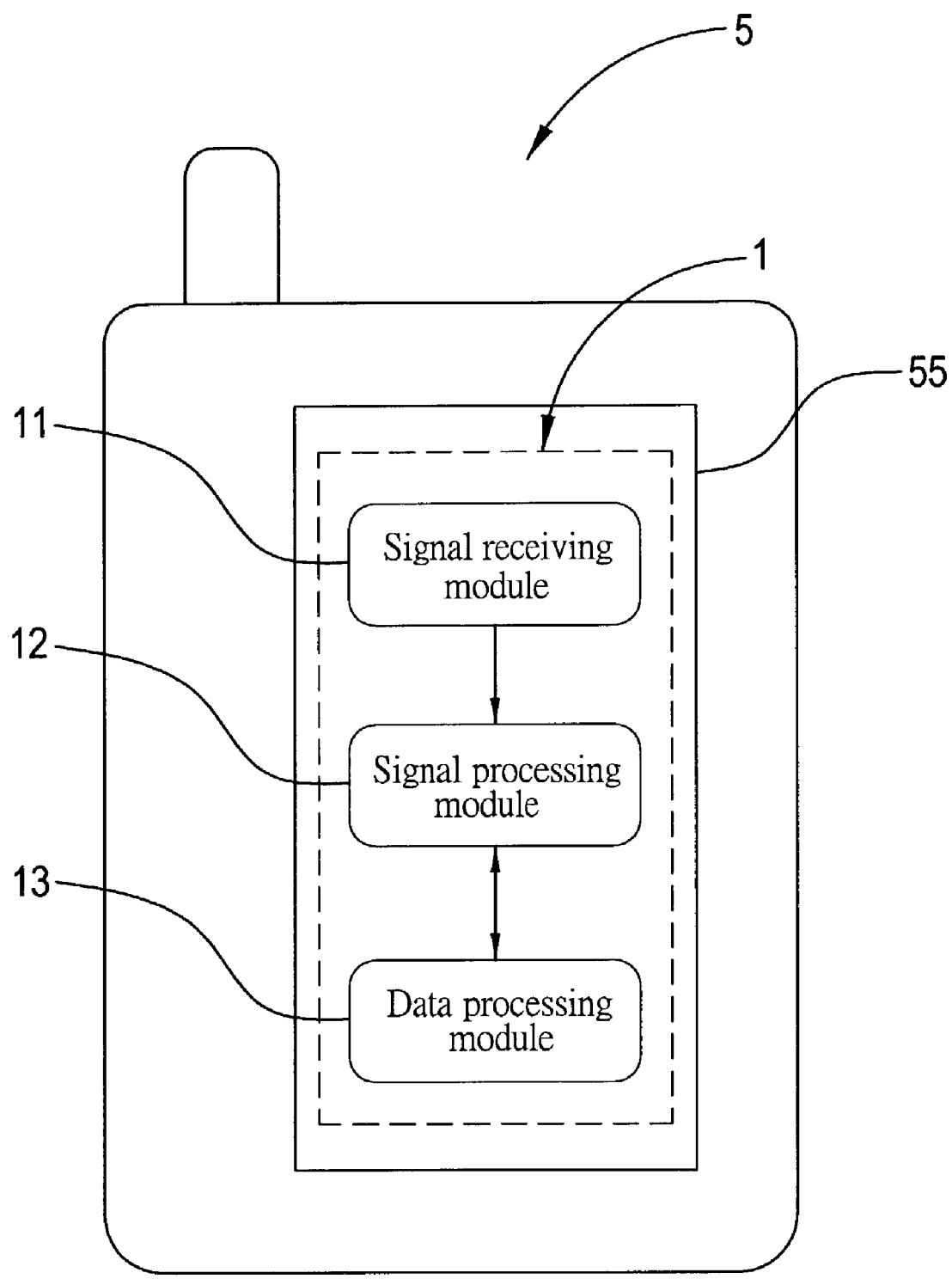
FIG. 2 is a schematic view showing the present invention is built in the cellular phone by means of SOC mode.

Referring to FIG. 1, this is a block diagram showing the scheme of the present invention in which a human physiological condition examination and processing device 1 is internally integrated with a cellular phone 5. Referring to FIG. 2, the drawing shows that the above said device 1 is built in the cellular phone 5 with SOC mode using a system-on-chip 55. The device 1 is composed of at least:

A signal receiving module 11 receives the signals of human physiological examination data from a skin surface contacting detector, an implanted biochip, or other portable measuring instruments by way of various wireless transmission modes such as infrared ray transmission, blue teeth transmission, or 820.11b transmission. The received signals are then inputted into a signal processing module 12.

The signal processing module 12 convents the inputted signals from the signal receiving module 11 into data signals and transfers said data into a data processing module 13.

The data processing module 13 analyses, compares, and stores said data signals inputted from the signal processing module 12, and transfers the resultant data to a cellular phone (5) functional module 51 as an output.

Upon receiving the signals of human physiological examination data coming from outside, the signal receiving module 11 and the data processing module 13 proceed to carry out signal conversion, data analyzing, comparing and storing, afterwards the resultant data are displayed and indicated on, or stored in the cellular phone 5, or even transmitted to a remote terminal for further investigation.

Figure 3:
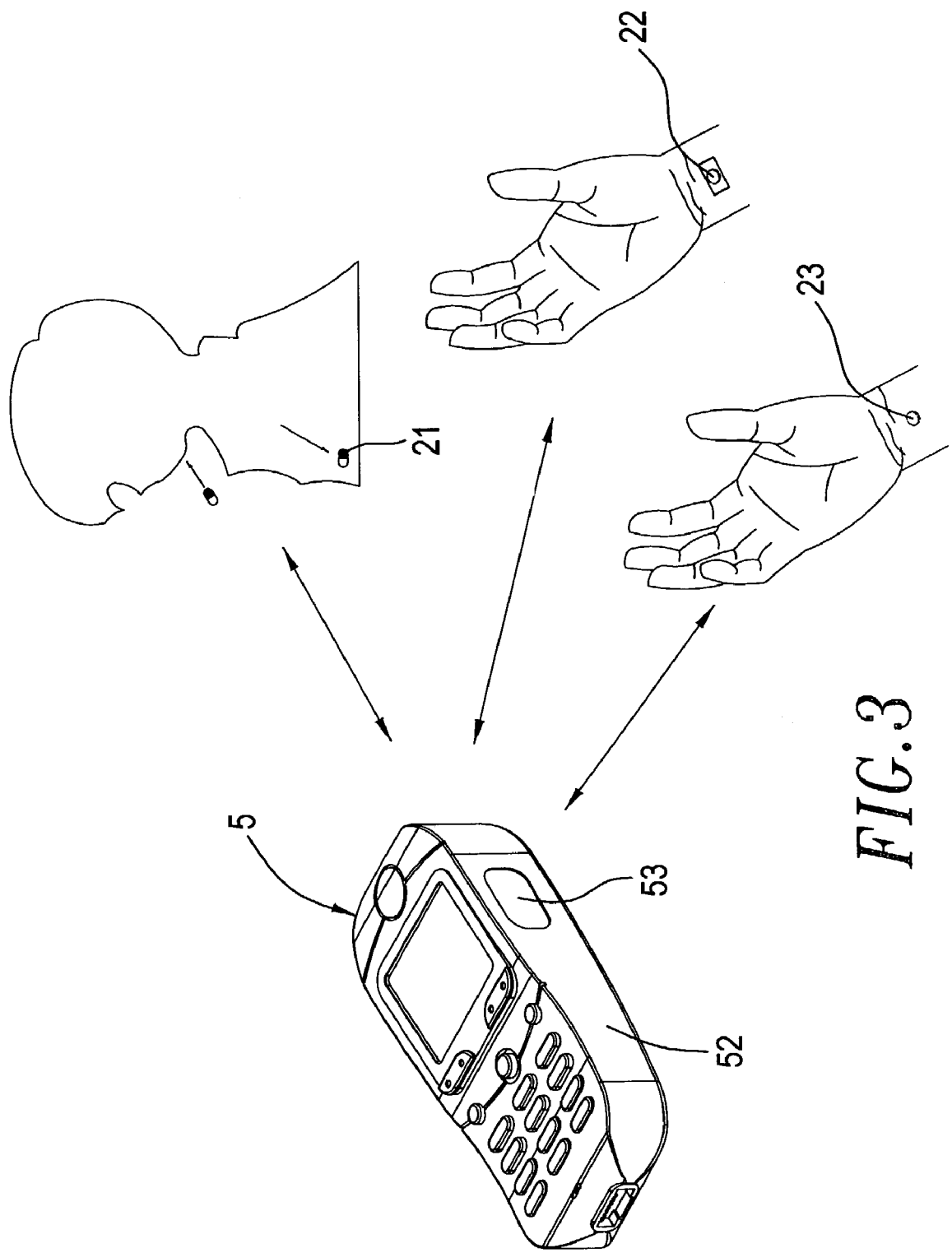
FIG. 3 is a schematic view showing how the cellular phone combined physiological condition examination and processing device of the present invention receives the signal from various biochips.

Referring to FIG. 3, this is a schematic view showing how the cellular phone combined device of the present invention receives the signals from various biochips. As shown in FIG. 3, the device 1 is internally integrated with the cellular phone 5, and a transmission element 53 emerged out of a phone body 52 serves as a wireless receiver to receive the human physiological condition signals from a biochip 21 swallowed in the patient esophagus, a biochip 22 adhered on the patient skin surface, and a biochip 23 implanted in the patient body through wireless transmission modes such as the infrared ray transmission, the blue teeth transmission, or the 820.11b wireless transmission, and then the resultant data after being processed are displayed or indicated on, or stored in the cellular phone 5, or even transmitted to a remote terminal for further investigation.

Figure 4:
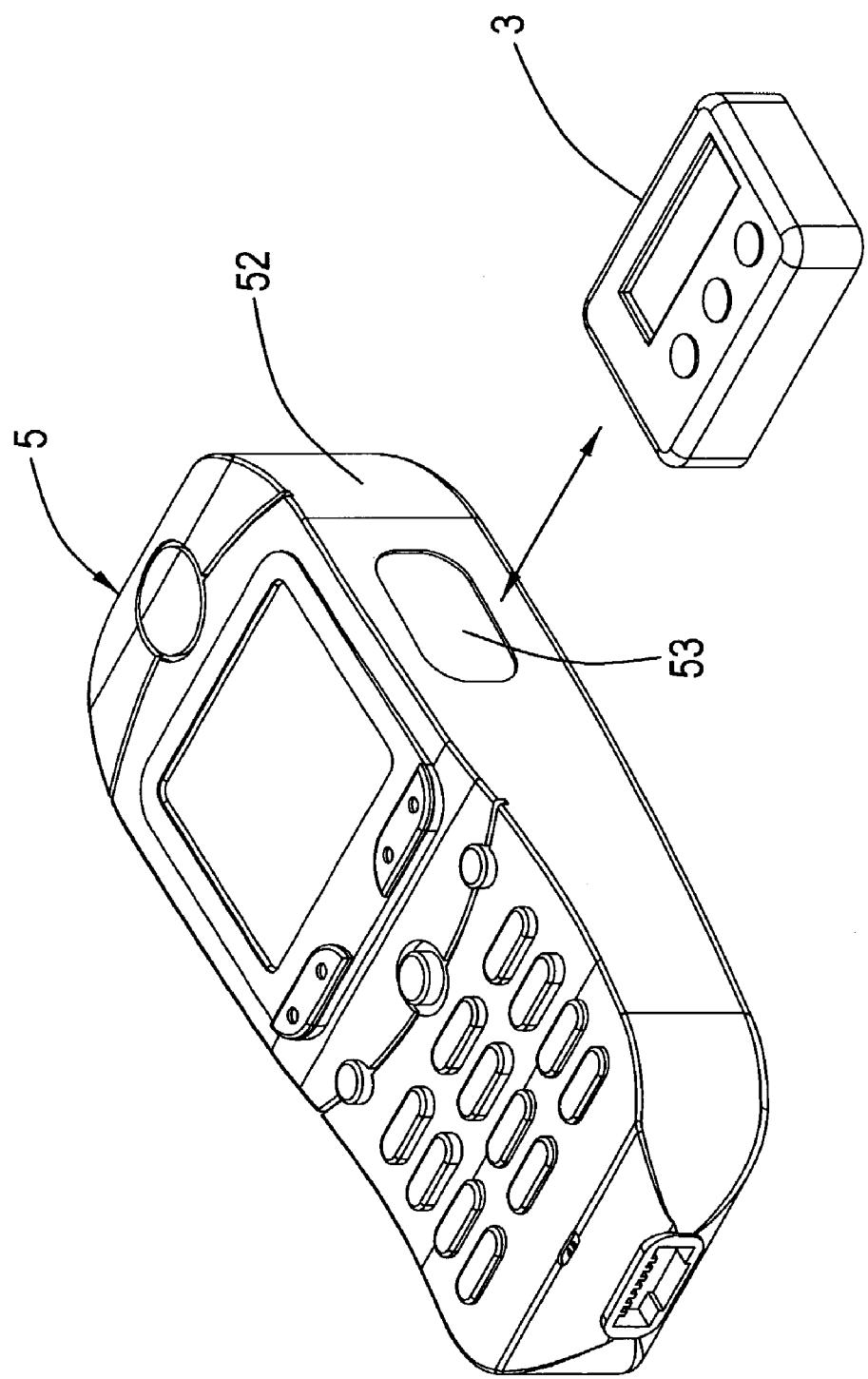
FIG. 4 is a schematic view showing how the cellular phone combined physiological condition examination and processing device of the present invention receives the signals from a human physiological condition detector.

Referring to FIG. 4, this is a schematic view showing how the cellular phone combined device of the present invention receives the signals from a human physiological condition detector 3, the detector 3 may be a skin surface contacting detector or a portable monitoring device. Similar to that shown in FIG. 3, the transmission element 53 emerged out of a phone body 52 serves as a wireless receiver to receive the human physiological condition data signals including temperature, blood pressure, pulse, cholesterol, RBC, GOT, GPT, CREA and BUN etc. provided by the detector 3. The wireless transmission modes include the infrared ray transmission, the blue teeth transmission, or the 820.11b wireless transmission, and then the resultant data after being processed are displayed or indicated on, or stored in the cellular phone 5, or even transmitted to a remote terminal for further investigation.

Note that in the present invention, the functional chip built in the cellular phone is a microelectronic IC chip to facilitate fabrication.

Figure 5:
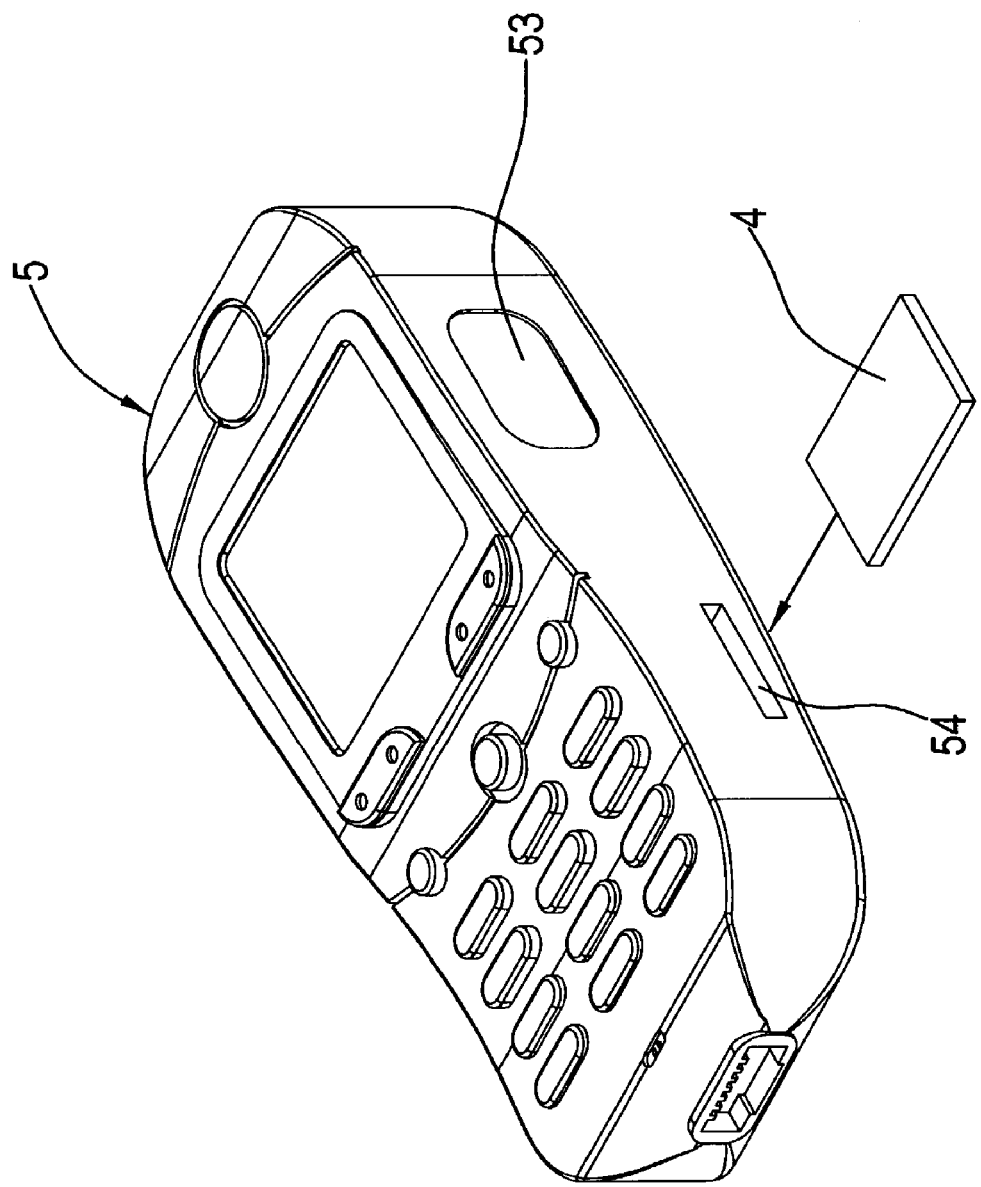
FIG. 5 is a schematic view showing how the physiological condition examination and processing device is externally attached to a cellular phone with a chip insertion mode.

Referring to FIG. 5, this is a schematic view showing how the cellular phone combined device of the present invention receives signals of human physiological condition from a chip externally inserted to the cellular phone. It can be observed that a chip 4 is inserted into an insertion slot 54 provided on the cellular phone 5. Similar to the way illustrated in FIGS. 3 and 4, the transmission element 53 is provided to the cellular phone 5 for serving as a wireless receiver to receive the human physiological condition signals from the biochips described in FIG. 3 or from the detector described in FIG. 4. The transmission modes and the data processing procedures are similar to those illustrated in FIGS. 3 and 4 therefore it is not necessary to be repeated herein.

Figure 6:
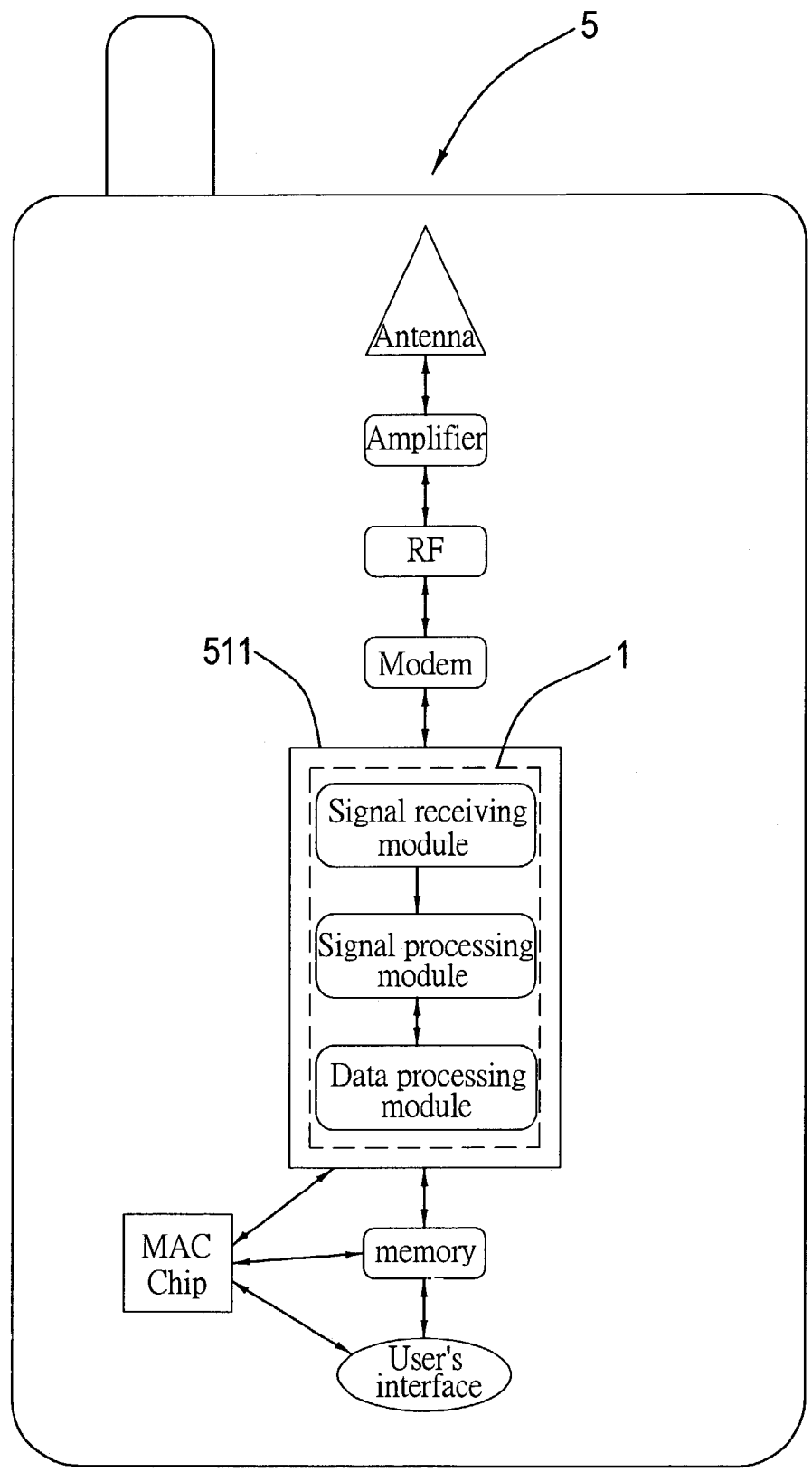

Referring to FIG. 6, a block diagram showing a basic frequency chip of a cellular phone in which the physiological condition examination and processing device is built in. As shown in FIG. 6, the physiological condition examination and processing device 1 can be built in a basic frequency chip 511 of the cellular phone 5. The basic frequency chip 511 is an operation center of the cellular phone including a microprocessor, a digital signal processor (DSP), and a memory. Those functions such as coding and encoding voice digital signals, periphery control and human-computer interface all belong to working scope of the basic frequency. Therefore, the expected effect can be achieved through integrating the physiological condition examination and processing device 1 into the basic frequency chip 511.

Furthermore, this device is conveniently compatible with various types of cellular phone, the aforesaid signal module, signal treating module and data processing module can be optionally incorporated in the cellular phone depending on the equipment which already being built therein.

Furthermore, this device is conveniently compatible with various types of cellular phones, the aforesaid signal module, signal treating module, and data processing module can be optionally incorporated in the cellular phone depending on the equipment which already being built therein.

From the above description, it can be clearly understood that the function of a cellular phone is widened by affixing the physiological condition examination and processing device. Moreover, the present invention is able to carry out physiological examination of human body very easily and efficiently without spending much money thereby greatly contributing to the human health and welfare.

Those who are skilled in the art will readily perceive how to modify the invention. Therefor, the appended claims are to be construed to cover all equivalent structures which fall within the true scope and spirit of the invention.

What is claimed is:

1. A cellular phone combined physiological condition examination and processing device internally integrated with said cellular phone comprising at least:
   a signal receiving module for receiving the signals of human physiological examination data from a monitoring instrument, a detector, or a biochip, and transmitting said received signals to a signal processing module;
   said signal processing module for converting said inputted signals from said signal receiving module into data signals and transferring said data signals to a data processing module;
   said data processing module for transferring the resultant data to a cellular phone functional module as an output after analyzing, comparing, and storing said data signals inputted from said signal processing module;
   each of said signal receiving, signal processing, and data processing modules being disposed in said cellular phone, and at least one of said monitoring instrument, detector, and biochip being disposed apart from said cellular phone in wireless communication with said signal receiving module;
   wherein upon receiving the signals of human physiological examination data coming from outside, said signal receiving module and said data processing module proceed to carry out signal conversion, data analyzing, comparing and storing, and the resultant data are provided to said cellular phone for further investigation.

2. A cellular phone combined physiological condition examination and processing device internally built in the main board of said cellular phone by way of system-on-a-chip (SOC) mode, comprising at least;
   a signal receiving module for receiving the signals of human physiological examination data front a monitoring instrument, a detector, or a biochip, and transmitting said received signals to a signal processing module;

said signal processing module for converting said inputted signals from said signal receiving module into data signals and transferring said data signals to a data processing module;

said data processing module for transferring the resultant data to a cellular phone functional module us an output after analyzing, comparing, and storing said data signals inputted from said signal processing module;

each of said signal receiving, signal processing, and data processing modules being disposed in said cellular phone, and at least one of said monitoring instrument, detector, and biochip being disposed apart from said cellular phone in wireless communication with said signal receiving module;

wherein upon receiving the signals of human physiological examination data coming from outside, said signal receiving module and said data processing module proceed to carry out signal conversion, data analyzing comparing and storing, and the resultant data are provided to said cellular phone for further investigation.

3. A cellular phone combined physiological condition examination and processing device externally attached to said cellular phone by inserting a memory card therein, comprising at least:

a signal receiving module for receiving the signals of human physiological examination data from a monitoring instrument, a detector, or a biochip, and transmitting said received signals to a signal processing module;

said signal processing module for converting said inputted signals from said signal receiving module into data signals and transferring said data signals to a data processing module;

said data processing module for transferring the resultant data to a cellular phone functional module as an output after analyzing, comparing, and storing said data signals inputted from said signal processing module;

each of said signal receiving, signal processing, and data processing modules being disposed in said cellular phone upon a chip card removably inserted therein, and at least one of said monitoring instrument, detector, and biochip being disposed apart from said cellular phone in wireless communication with said signal receiving module;

wherein upon receiving the signals of human physiological examination data coming from outside, said signal receiving module and said data processing module proceed to carry out signal conversion, data analyzing, comparing and storing, and the resultant data are provided to said cellular phone for further investigation.

4. A cellular phone combined physiological condition examination and processing device integrally built in a basic frequency chip of the cellular phone, comprising at least:

a signal receiving module for receiving the signals of human physiological examination data from a monitoring instrument, a detector, or a biochip, in wireless transmission mode, and transmitting said received signals to a signal processing module;

said signal processing nodule for converting said inputted signals from said signal receiving module into data signals and transferring said data signals into a data processing module;

said data processing module for transferring the resultant data to a cellular phone functional module as an output after analyzing, comparing, and storing said data signals inputted from said signal processing module;

each of said signal receiving, signal processing, and data processing modules being disposed in said cellular phone, and at least one of said monitoring instrument, detector, and biochip being disposed apart from said cellular phone in wireless communication with said signal receiving module;

wherein upon receiving the signals of human physiological examination data coming from outside, said signal receiving module and said data processing module proceed to carry out signal conversion, data analyzing, comparing and storing, and the resultant data are provided to said basic frequency chip of the cellular phone for further monitoring the human physiological condition.

5. The device as any of claims 1 to 4, wherein said resultant human physiological examination data are transmitted in wireless modes such as infrared ray transmission, blue teeth transmission, or 820.11b wireless transmission.

6. The device as any of claims 1 to 4, wherein said resultant human physiological examination data are displayed on said cellular phone.

7. The device as any of claims 1 to 4, wherein said resultant human physiological examination data are indicated on cellular phone as warning.

8. The device as any of claims 1 to 4, wherein said resultant human physiological examination data are stored in said cellular phone.

9. The device as any of claims 1 to 4, wherein said resultant human physiological examination data are transmitted to a remote terminal for further investigation.

10. The devices as any of claims 1 to 4, wherein said device is compatible with various types of cellular phone, said signal receiving module, said signal treating module and said data processing module are able to be optionally incorporated in said cellular phone depending on the equipment which already being built therein.

* * * * *

UNITED STATES PATENT AND TRADEMARK OFFICE
CERTIFICATE OF CORRECTION

| | | |
|---|---|---|
| PATENT NO. | : 7,031,745 B2 | Page 1 of 1 |
| APPLICATION NO. | : 10/435080 | |
| DATED | : April 18, 2006 | |
| INVENTOR(S) | : Ein-Yiao Shen | |

It is certified that error appears in the above-identified patent and that said Letters Patent is hereby corrected as shown below:

Title page, item (76), under "Inventor", delete "Yuan-Yao Shen" and insert -- Ein-Yiao Shen --.

Signed and Sealed this

Twentieth Day of December, 2011

David J. Kappos
*Director of the United States Patent and Trademark Office*